United States Patent [19]

Weber

[11] Patent Number: 5,275,706
[45] Date of Patent: Jan. 4, 1994

[54] METHOD AND APPARATUS FOR CONTINUOUS, CARRIER-FREE DEFLECTION ELECTROPHORESIS

[76] Inventor: Gerhard Weber, Margaritenweg 23, 8011 Kirchheim, Fed. Rep. of Germany

[21] Appl. No.: 981,607

[22] Filed: Nov. 25, 1992

[30] Foreign Application Priority Data

Nov. 29, 1991 [DE] Fed. Rep. of Germany ....... 4139472

[51] Int. Cl.$^5$ .................... G01N 27/26; G01N 27/447
[52] U.S. Cl. ................ 204/180.1; 204/299 R; 204/301
[58] Field of Search ................ 204/299R, 301, 180.1, 183.2, 183.3

[56] References Cited

U.S. PATENT DOCUMENTS

| | | | |
|---|---|---|---|
| 2,878,178 | 3/1959 | Bier | 204/180 |
| 3,519,549 | 7/1970 | Grassmann et al. | 204/180.1 X |
| 3,869,365 | 4/1975 | Sunden | 204/183.3 |
| 4,061,560 | 12/1977 | Hannig et al. | 204/299 R |
| 4,309,268 | 1/1982 | Richman | 204/183.2 |

Primary Examiner—Donald R. Valentine
Assistant Examiner—John S. Starsiak, Jr.
Attorney, Agent, or Firm—Marshall, O'Toole, Gerstein, Murray & Borun

[57] ABSTRACT

In carrier-free continuous deflection electrophoresis problems are encountered in the collection of fractions and it is necessary to use hose pumps with a number of channels corresponding to the number of fractions desired. This arrangement is not only elaborate and susceptible to disturbance, for a great variety of reasons, but even more importantly it necessitates a certain minimal flow velocity within the separation chamber. To improve the effectiveness of separation it is proposed by the present invention to adjust the outflow rate from the separation chamber in the region of its outlet end by introducing an additive medium with a predetermined flow rate in countercurrent to the flow direction of the separation and sample media. In this way the time the sample spends in the electric field and hence the corresponding separation effect is considerably increased.

14 Claims, 3 Drawing Sheets ent invention relates to a method and apparatus for continuous, carrier-free deflection electrophoresis.

METHOD AND APPARATUS FOR CONTINUOUS, CARRIER-FREE DEFLECTION ELECTROPHORESIS

FIELD OF THE INVENTION

The present invention relates to a method and apparatus for continuous, carrier-free deflection electrophoresis.

DESCRIPTION OF THE PRIOR ART

The basic principles of continuous electrophoresis, which employs a liquid carrier, have long been known and have been published, for example in the 1969 Yearbook of the Max Planck Society at pp. 117–137, which also cites additional literature. A commonly used abbreviation for this technique is FFE (free-flow electrophoresis).

FFE separation methods are used to isolate ions of arbitrary molecular weight, including bioparticles, because electrophoretic migration in an electric field is independent of whether a charge is borne by a molecule or a particle and of whether it is acquired by addition or adsorption of foreign ions. The method is used both for preparative and for analytical separation.

In the following, the known methods and the known apparatus are discussed with reference to FIG. 3.

In this drawing, a separation chamber is illustrated schematically with reference numbers as indicated. At an upper inlet end 13 of the separation chamber 10 there is an inlet opening 15, which communicates by way of a medium conduit 22 with a reservoir 19 mounted at a higher level. Separation medium can be introduced through this inlet opening 15. Also opening into the separation chamber 10 at its upper 13 are conduits 23 and 24, which lead to additional medium containers 20 and 21 by way of a common media pump 25 such as a hose pump.

A sample inlet 16 near the inlet end 13 is connected to a sample vessel 26 by way of a sample conduit 27 and a bubble trap 28.

At the two sides of the separation chamber 10 membranes 8 are provided which isolate electrodes 11 and 12 from the actual separation space.

At the lower outlet end 14 of the separation chamber 10 a plurality of fraction outlets 17a–17n is provided; these outlets communicate with a fraction vessel 29 by way of fraction conduits 30a–30n which pass through a fraction pump 9 such as a hose pump.

The functional principles of this arrangement will now be discussed.

In known methods and apparatus the media, in particular the separation medium and the sample, are introduced into the separation space under gravity, which takes a relatively long time. Furthermore, it is difficult to keep the relative rates of travel constant, which considerably affects the precision of the separation.

In simultaneous fractionation, the fractions are usually collected by means of pumps. Hence if, for example, 90 fractions are desired, a pump must be used that has 90 channels operating completely independently of one another. In this case it is necessary to ensure that the volume flow rate is the same in all channels. For this purpose hose pumps are used, the relative propulsion rates of which are defined by the individual hoses in the individual channels. This means, however, that the volume flows are determined by the inside diameters of the individual hoses. This inside diameter changes in the course of time, which has a considerable influence in systems for long-term operation such as are of interest here. Given the necessarily large number of hoses or fraction channels, even if silicone material of the lowest hardness is used, forces are exerted against the bearings and shafts of the pump that considerably shorten their useful life. Even though the silicone, which is the only material suitable for this purpose, has a small wall thickness it nevertheless gives only a few hours of operation. The resulting continual replacement of the hoses is labor and cost intensive.

The "separation effect" of the fractionation is closely related to the time the sample spends in the electric field and hence to the flow velocity in the separation chamber. In a given separation chamber, therefore, the separation effect is limited by the fact that the volume flow in the individual channels of the fractionation pump cannot be made arbitrarily small. Furthermore, as the volume flow decreases, the fluctuations in volume flow increase, which leads to oscillating flow rates in the separation chamber and thus, in turn, to less effective separation.

Another problem with conventional FFE is that it is essential to prevent appreciable lowering of the pressure in the separation chamber, because otherwise gas or air bubbles will form and considerably impair the results of the separation process. This problem cannot be entirely solved even by introducing the media (except for one) by means of volumetric-propulsion pumps, because even here the residual pulsations mentioned above reduce the effectiveness of separation.

As previously mentioned, the material used for the hoses in the fractionation pump plays a further role in the process. The only sufficiently soft material for the hoses is silicone; a longer-lasting material such as PTFE is unusable because it is too hard.

In the long-term process of interest here, a further problem is presented by changes which occur in the membranes isolating the electrodes from the actual separation space. These effects are especially disturbing when a method of continuous isoelectric focussing is being used.

SUMMARY OF THE INVENTION

The present invention is directed to the problem of improving the separation achievable in the long-term operation of apparatus for continuous, carrier-free deflection electrophoresis.

According to a first aspect of the present invention there is provided a method for continuous, carrier-free deflection electrophoresis, comprising the steps of providing a separation chamber through which at least one separation medium as carrier and a sample medium to be investigated flow at a substantially constant delivery rate from an inlet end to an outlet end thereof, generating an electric field by means of electrodes across the separation chamber to separate spatially the sample medium into fractions, and collecting the fractions at a substantially constant outflow rate, and wherein the improvement comprises delivering an additive medium to the separation chamber at a predetermined flow rate in countercurrent to the separation and sample media in order to adjust the outflow rate from the separation chamber in the region of its outlet end.

According to a second aspect of the present invention there is provided an apparatus for continuous, carrier-free deflection electrophoresis comprising a separation chamber with an inlet end, which defines at least one inlet opening through which a separation medium can be introduced at a substantially constant flow rate and at least one sample inlet through which a sample medium can be introduced at a substantially constant flow rate, and an outlet end, which defines a plurality of fraction outlets to collect fractions of the sample medium at a substantially constant flow rate, electrodes located within the separation chamber, and membranes for the electrodes, and wherein the improvement comprises the provision of of an additive inlet at the outlet end of the separation chamber through which an additive medium can be introduced into the separation chamber so as to flow in countercurrent to the separation and sample media.

Fundamental to the present invention is the adjustment of flow and pressure conditions, and hence of the outflow rate of fractions from the separation chamber, by the supply of an additive medium with a predetermined flow rate. This additive medium flows in countercurrent to the separation and sample media so that in the separation chamber the same media flow as previously, namely the separation medium with the sample medium, but during collection of the fractions the additive medium is collected along with them. In this way, the flow rate in the separation chamber (in the gap) can, in principle, be made arbitrarily low, even though continuous collection of "fractions" (in this case, of course, at lower concentrations) occurs. The separation effect can thus be considerably enhanced.

It is advantageous for the additive medium to comprise a separation medium. To it can be added a reagent that reacts with at least one of the fractions, in order to determine the reaction or its result. The addition of the additive medium and the associated increase in flow velocity between the fraction outlet that is the collection point in the separation chamber and a corresponding detector in the fraction conduit ensures a considerable shortening of the delay time.

All the media are introduced by way of volumetric propulsion pumps such as hose pumps, whereas collection is a purely passive process, without a fraction pump. Hence, a multichannel hose pump with all the problems described above is no longer required. When the present invention is employed, the fraction conduits or hoses can be made of any material and retain their mechanical characteristics throughout long periods of use because they are under no mechanical stress. To fix the volume flow rates of the fractions it is not necessary, as previously, to make the cross-sections of the conduit lumens absolutely identical. Instead, when the present invention is employed it is merely a matter of making the resistances to flow identical, which can be done with tubes of different inside diameters by varying their lengths accordingly. A concomitant result is that a negative pressure can never develop in the separation chamber; on the contrary, there is always a certain amount of excess pressure.

Another subsidiary aspect of the present invention, which can also be applied with the same advantages to conventional FFE methods or FFE apparatus, substantially constant volume flows of membrane media are introduced into the separation chamber at its periphery in such a way that the membrane surfaces toward the separation chamber lie within the membrane media and are isolated by them from the separation medium and the sample in the rest of the separation space by virtue of the interfaces between the membrane media currents and the separation medium plus sample current which effectively form liquid membranes. Different membrane media are supplied in the anodal and cathodal regions to reduce or suppress the accumulation of ions at one membrane and the depletion of ions at the other membrane. Thus, the media keep the membrane properties constant and this is especially important for long-term operation.

The conductivities of the membrane media are preferably adjusted to substantially the same values, such as that of the electrode buffer conventionally surrounding the electrodes. In this way a warming of the membranes and of the surrounding regions, with a concomitant change in the electric field, is effectively prevented.

DESCRIPTION OF THE PREFERRED EMBODIMENTS

In the following description, the same reference numbers are used for the same components and those with the same function which occur in the embodiments described with reference to both FIG. 1 and FIG. 2 as well as those previously described with reference to FIG. 3.

Figure 1:
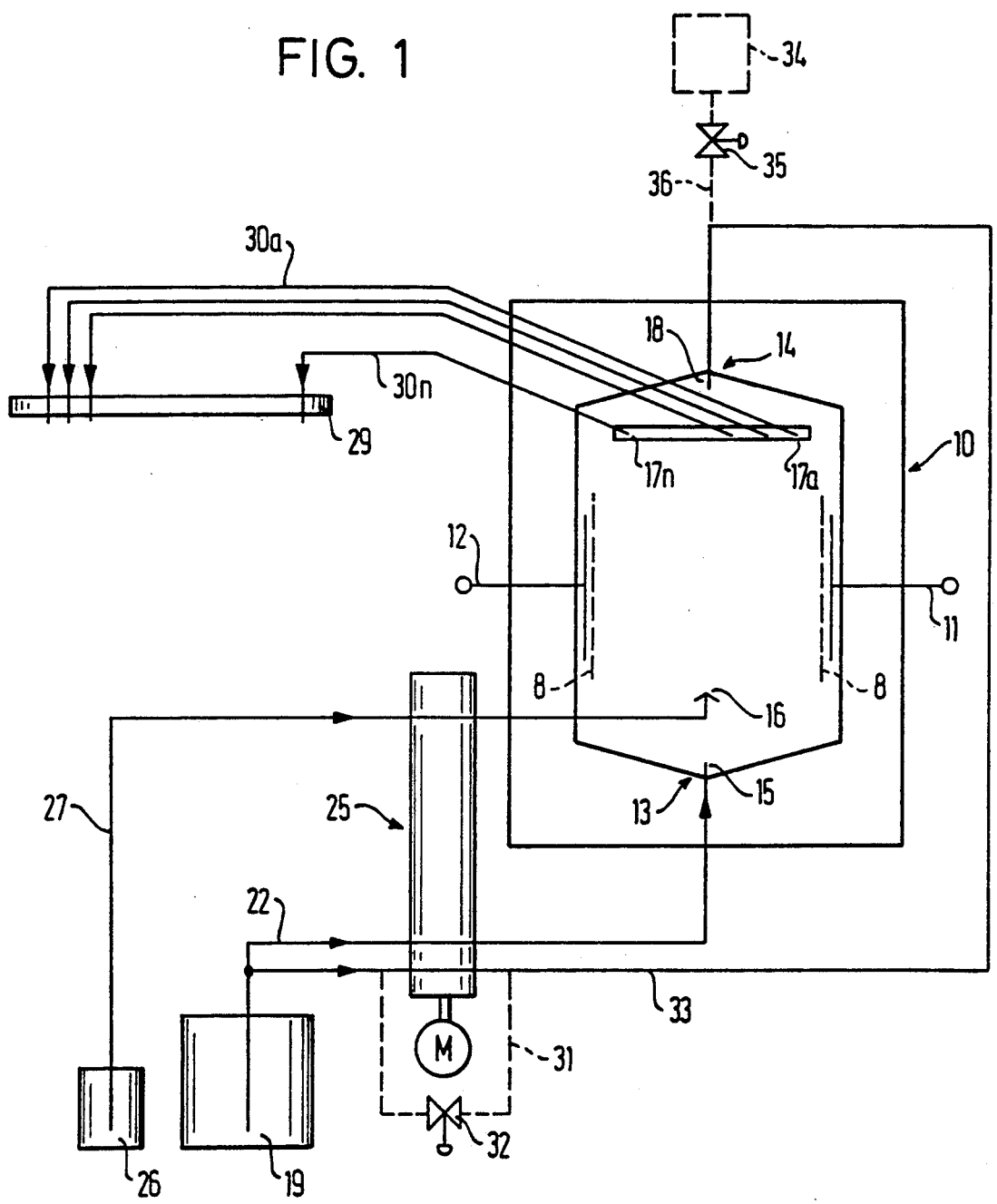
FIG. 1 is a diagram showing schematically a first embodiment of the invention.
Figure 2:
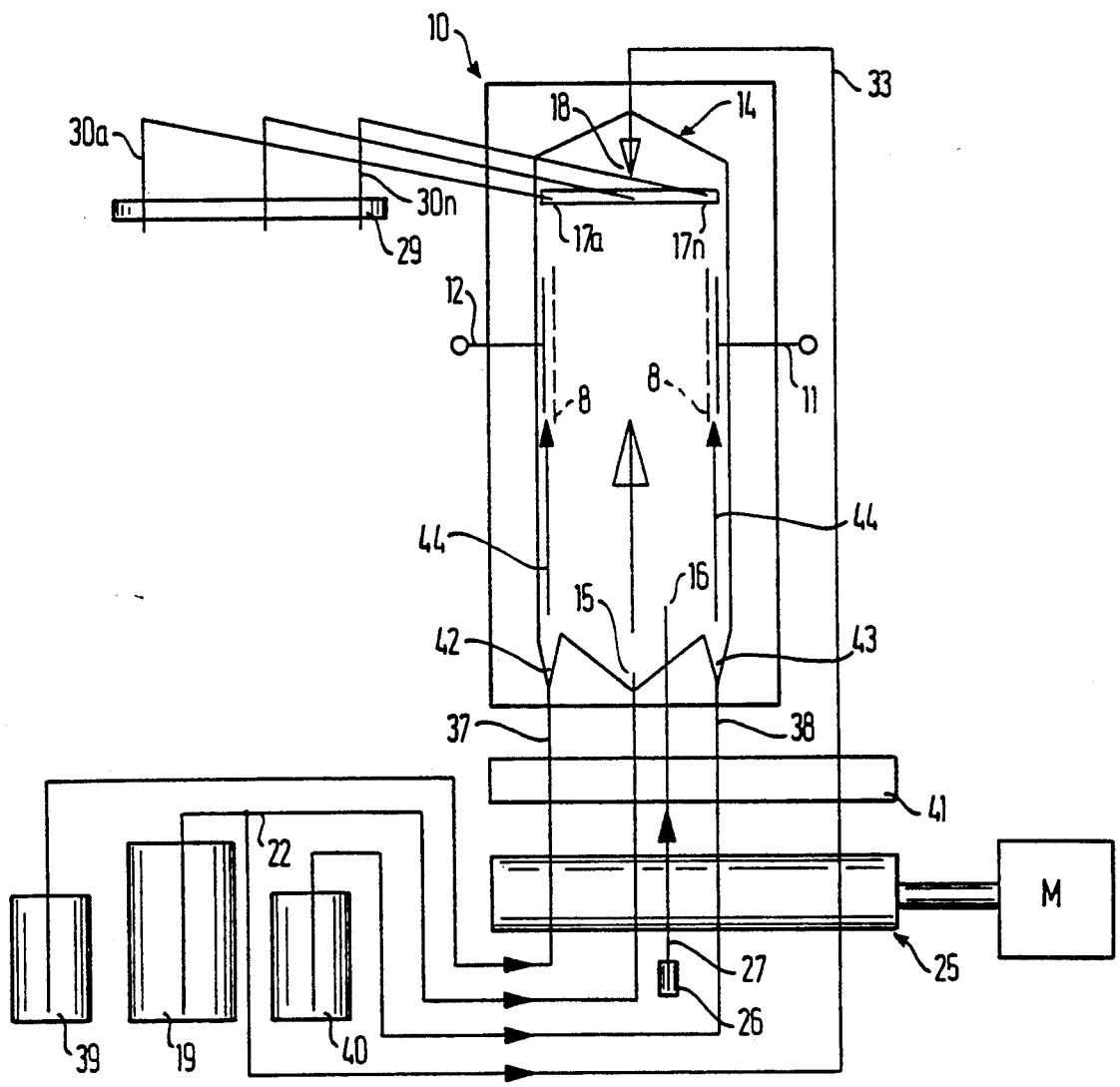
FIG. 2 is a diagram, similar to FIG. 1 but showing a second embodiment of the invention.

In the embodiment of the invention shown in FIG. 1, a separation chamber 10 comprises an inlet end 13 at the bottom and into it opens a media conduit 22 by way of an inlet opening 15. The media conduit 22 leads to a reservoir 19.

Near the inlet end 13 is a sample inlet 16, which is connected to a sample vessel 26 by way of a sample conduit 27.

From the media conduit 22, an additive conduit 33 branches off and leads to an outlet end 14 at the top of the separation chamber 10, into which the additive conduit 33 opens by way of an additive inlet 18.

The sample conduit 27, the separation media conduit 22 and the additive conduit 33 pass through a media pump 25, so that these three media are transported in a precisely equal flow relationship.

To adjust the flow of the additive medium, in the embodiment illustrated here, a bypass conduit 31 with a control valve 32 is provided, so that part of the additive stream propelled forward by the pump can be returned.

In the separation chamber 10, as in conventional apparatus, electrodes 11 and 12 are positioned behind membranes 8.

Near the upper outlet end 14 there are fraction outlets 17a–17n, which communicate with a fraction vessel 29 by way of fraction conduits 30a–30n. No pump is provided for these conduits.

In the embodiment shown here, a reagent container 34 can be provided (indicated in dashed lines), which leads to the additive conduit 33 by way of a control valve 35 and a conduit 36. The necessary driving pressure can be provided by gravity, by an additional volumetric pump or by passing the reagent conduit 36 through the pump 25.

In operation, the separation medium and the sample are continuously introduced to the separation chamber 10 through the conduits 22 and 27, respectively, by means of the pump 25, so that both media flow toward the outlet end 14. As the flowing media pass through the electric field generated by electrodes 11 and 12, the components of the sample are deflected according to the various charges of the ions or particles and according to their characteristic frictional resistances, on the way to the fraction outlets 17a–17n.

At the same time, an additive medium which in the present case consists of separation medium, is introduced through the conduit 33 and the additive inlet 18 of the separation chamber 10. Because the fraction outlets 17a–17n are situated between the additive inlet 18 and the lower inlets, namely the inlet opening 15 and the sample inlet 16, the additive medium flows in countercurrent to the separation medium and the sample it contains. These two (or three) volume flow entities flow simultaneously through the fraction outlets 17a–17n, the fraction conduits 30a–30n being so dimensioned with respect to diameter and length that the resistances to flow at the fraction outlets 17a–17n are substantially the same. This arrangement ensures that the amount of additive added to the separation medium with the sample it contains, or to its fraction, is substantially the same at all the fraction outlets 17a–17n. This in turn means that, given a constant volume flow (volume per unit time) through the fraction conduits 30a–30n, the flow velocity through the separation chamber 10 between the electrodes 11,12 can be made high or low, depending on the volume flow of the additive in relation to the sum of the other volume flows. The time the "sample elements" spend in the electric field, and thus the precision of separation, can be adjusted in this way. This is especially important in the case of continuous isoelectric focussing, in which the flow rates are lower by about a factor of 5 than in the case of the FF-zone electrophoresis that has previously been employed almost exclusively.

By the addition of the additive medium in countercurrent, it is possible to avoid excessively small cross-sectional areas or excessive length of the fraction conduits 30a–30n, so that there is no danger of obstruction in hoses with inadequate inside diameters when precipitation or aggregation of the sample or its components occurs. A large "dead" volume in the fractionation apparatus can also be avoided in this way. In contrast, even with the lowest flow rates in the separation space a fractionation apparatus with favorable lumen and length of the hose elements can be used, so that rapid on-line detection is combined with control of the separation process to achieve a "stationary" separation profile in long-term experiments.

The introduction of a reagent, by the means 34–36, together with the additive medium so that it also flows in countercurrent, keeps the reagent from contacting the sample fraction until the latter has almost reached the fraction outlets 17a–17n. In this way there is no interference with fractionation in the electric field but a reaction or the reaction product can be detected with suitable apparatus just before (or after) the fraction outlet.

Figure 3:
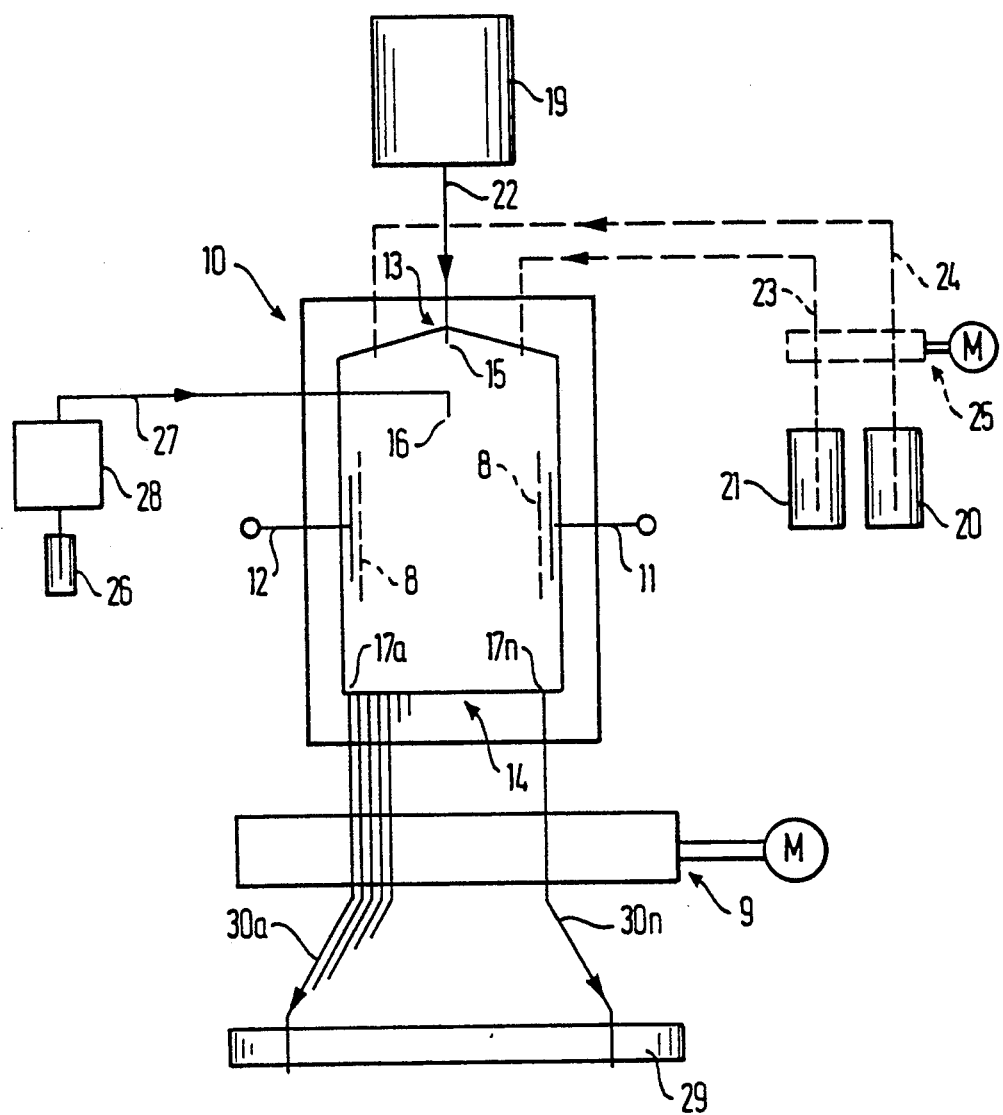
FIG. 3 is a diagram showing schematically a conventional apparatus.

If one compares the apparatus in accordance with the invention as shown in FIG. 1 with conventional apparatus as shown in FIG. 3, a first difference that is immediately obvious is that the invention eliminates the multichannel pump 9, which amounts to a considerable simplification. A further difference is that a low pressure can never develop within the separation chamber 10.

A second embodiment of the present invention will now be described with reference to FIG. 2.

This embodiment of the present invention is distinguished from that shown in FIG. 1 by the provision in the peripheral region of the separation chamber 10 of a first and a second membrane media inlet 42 and 43, respectively, which are respectively connected to membrane media containers 39 and 40 by way of respective conduits 37 and 38. All the conduits leading into the separation chamber 10 pass through a pulsation attenuator 41 after leaving the media pump 25.

The inlets 42, 43 are arranged in such a way that membrane media currents 44 (indicated by arrows in FIG. 2) develop, which flow through the separation chamber 10 along the membranes 8 and "isolate" the membranes 8 from the remainder of the separation space. Through these membrane media inlets 42, 43 stabilization media are introduced, which compensate ion redistribution effects deriving from the known selectivity properties of membranes in ion transport; that is, they prevent the accumulation of ions associated with one of the electrodes 11, 12 at one of the membranes 8 and suppress ion depletion at the other membrane 8, depending on the electrode polarity. As a result, the otherwise unavoidable alteration of the membrane properties during prolonged operation of the apparatus is avoided, so that its influence on the separation effectiveness of the method is substantially eliminated.

The introduced stabilization or membrane medium at its interface with the remaining content of the separation space forms, so to speak, a liquid membrane and delivers across these two interfaces all the necessary ions in the correct absolute and relative concentration. The chosen stabilization medium will preferably have a conductivity similar to that of the electrode buffer used, so that there is no abrupt change in resistance across the membrane and hence no warming occurs.

The method modified in this way (or the apparatus thus modified) is particularly advantageous for the application of isoelectric focussing, where previously selective ion transport at conventional membrane partitions caused extreme interference. At this juncture it should also be mentioned that this particular embodiment of the invention is also suitable for application to apparatus as shown in FIG. 1, in which the same problem occurs. This modification is thus a solution, in accordance with the invention, of one of the problems discussed initially and can be employed independently or as a supplementary measure.

It can be seen from the above that the method and apparatus in accordance with the invention offer many advantages because of the elimination of the fraction pump that was previously required. One of them is that this feature makes sterile operation possible by a simple means, since sterile filters can be provided on the pressure side of the apparatus.

What is claimed is:

1. A method for continuous, carrier-free deflection electrophoresis, comprising the steps of
providing a separation chamber through which at least one separation medium as carrier and a sample medium to be investigated flow at a substantially constant delivery rate from an inlet end to an outlet end thereof,
generating an electric field by means of electrodes across the separation chamber to separate spatially the sample medium into fractions, and collecting the fractions at a substantially constant outflow rate, and wherein the improvement comprises delivering an additive medium to the separation chamber at a predetermined flow rate in countercurrent to the separation and sample media in order to adjust the outflow rate from the separation chamber in the region of its outlet end.

2. A method as claimed in claim 1, wherein the additive medium is the same as the separation medium.

3. A method as claimed in claim 1, comprising the additional step of adding to the additive medium at least one reagent, which reacts with at least one of the fractions, so that at least one of the reaction and its result can be detected.

4. A method as claimed in claim 1, wherein the delivery of all media to the separation chamber is by means of a volumetric-propulsion pump.

5. A method as claimed in claim 1, wherein isolation membranes are provided for the electrodes and the method comprises the additional step of introducing substantially constant volume flows of membrane media into the separation chamber at its periphery in such a way that the membrane surfaces toward the separation chamber lie within the membrane media and are isolated by them from the separation medium and the sample medium in the rest of the separation space by virtue of the interfaces between the membrane media currents and the separation medium plus sample medium current which effectively form liquid membranes, different membrane media being supplied in the anodal and cathodal regions to reduce or suppress the accumulation of ions at one membrane and the depletion of ions at the other membrane.

6. A method as claimed in claim 5, comprising the additional step of adjusting the conductivity of the membrane media so that it is substantially the same as that of an electrode buffer surrounding the electrodes.

7. An apparatus for continuous, carrier-free deflection electrophoresis comprising a separation chamber with an inlet end, which defines at least one inlet opening through which a separation medium can be introduced at a substantially constant flow rate and at least one sample inlet through which a sample medium can be introduced at a substantially constant flow rate, and an outlet end, which defines a plurality of fraction outlets to collect fractions of the sample medium at a substantially constant flow rate, electrodes located within the separation chamber, and membranes for the electrodes, and wherein the improvement comprises the provision of of an additive inlet at the outlet end of the separation chamber through which an additive medium can be introduced into the separation chamber so as to flow in countercurrent to the separation and sample media.

8. An apparatus as claimed in claim 7, wherein the additive inlet is connected to a conduit for the separation medium which leads to the inlet opening.

9. An apparatus as claimed in claim 7, wherein means are provided to deliver a reagent to the additive inlet.

10. An apparatus as claimed in claim 7, wherein hoses with predetermined flow cross-sections and resistances to flow are connected to the fraction outlets.

11. An apparatus as claimed in claim 7, wherein the separation chamber defines membrane media inlets which open into the separation chamber at its periphery in such a way that membrane media currents can be produced in the peripheral regions of the separation chamber to isolate the membranes from the separation medium and sample medium, the interfaces between the membrane media currents and the separation and sample media current effectively forming liquid membranes.

12. An apparatus as claimed in claim 7, comprising pump means located ahead of the inlet openings and inlets to the separation chamber.

13. An apparatus as claimed in claim 12, wherein the pump means comprises a single multichannel pump.

14. An apparatus as claimed in claim 12, wherein the pump means comprises a multiple-hose pump.

* * * * *